US008200307B2

(12) United States Patent
Caduff et al.

(10) Patent No.: US 8,200,307 B2
(45) Date of Patent: Jun. 12, 2012

(54) METHOD AND DEVICE FOR DETERMINING A PARAMETER OF LIVING TISSUE

(75) Inventors: Andreas Caduff, Zurich (CH); Pascal Truffer, Zurich (CH); Yaroslav Ryabov, Kazan (RU); Yuri Feldman, Jerusalem (IL); Alexander Puzenko, Jerusalem (IL)

(73) Assignee: Biovotion AG, Zurich (CH)

( * ) Notice: Subject to any disclaimer, the term of this patent is extended or adjusted under 35 U.S.C. 154(b) by 1237 days.

(21) Appl. No.: 11/596,565

(22) PCT Filed: Jun. 7, 2004
(Under 37 CFR 1.47)

(86) PCT No.: PCT/CH2004/000345
§ 371 (c)(1),
(2), (4) Date: Sep. 28, 2007

(87) PCT Pub. No.: WO2005/120332
PCT Pub. Date: Dec. 22, 2005

(65) Prior Publication Data
US 2008/0057526 A1    Mar. 6, 2008

(51) Int. Cl.
*A61B 5/05* (2006.01)
(52) U.S. Cl. .................. 600/345; 600/347; 600/365
(58) Field of Classification Search .............. 600/316, 600/345–347, 365; 435/4; 422/50
See application file for complete search history.

(56) References Cited

U.S. PATENT DOCUMENTS

| | | |
|---|---|---|
| 3,654,072 A | 4/1972 | Massa |
| 4,509,531 A | 4/1985 | Ward |
| 5,353,802 A | 10/1994 | Ollmar |
| 6,070,093 A | 5/2000 | Oosta et al. |
| 6,356,776 B1 | 3/2002 | Berner et al. |
| 6,565,509 B1 | 5/2003 | Say et al. |
| 2003/0153821 A1 | 8/2003 | Berner et al. |
| 2003/0216663 A1* | 11/2003 | Jersey-Willuhn et al. .... 600/547 |

(Continued)

FOREIGN PATENT DOCUMENTS

| | | |
|---|---|---|
| GB | 2 033 575 A | 5/1980 |
| GB | 2 055 206 A | 2/1981 |
| GB | 2 100 864 A | 1/1983 |

(Continued)

OTHER PUBLICATIONS

South Korean Office Action received on Nov. 25, 2010 in co-pending Korean Patent Appln. No. 10-2006-7025637.

(Continued)

*Primary Examiner* — Patricia Mallari
*Assistant Examiner* — Michael D'Angelo
(74) *Attorney, Agent, or Firm* — Ladas & Parry LLP

(57) ABSTRACT

A device for measuring a glucose level or some other parameter of living tissue that affects the dielectric properties of the tissue is disclosed. The device comprises an electrode arrangement (5) having a plurality of electrodes (5-*i*). The signal from a signal source (31) can be applied to the electrode arrangement via a switching assembly (39). The switching assembly (39) is designed to selectively connect a first and a second pattern of the electrodes (5-*i*) to the signal source, thereby generating a first and a second electrical field with different spatial distribution in the tissue. By using a differential method which relies on measuring the impedance of the electrode arrangement (5) for each field and on suitable subtraction of the measured results, surface effects can be reduced and the focus of the measurement can be offset to a point deeper inside the tissue.

7 Claims, 2 Drawing Sheets

U.S. PATENT DOCUMENTS

| | | | |
|---|---|---|---|
| 2004/0039254 A1 | 2/2004 | Stivoric et al. | |
| 2004/0147819 A1* | 7/2004 | Caduff et al. | 600/316 |
| 2006/0264730 A1 | 11/2006 | Stivoric et al. | |
| 2006/0270942 A1 | 11/2006 | McAdams | |
| 2007/0161881 A1* | 7/2007 | Ollmar et al. | 600/347 |

FOREIGN PATENT DOCUMENTS

| | | |
|---|---|---|
| WO | 93/18395 | 9/1993 |
| WO | 93/18402 | 9/1993 |
| WO | 99/39627 | 8/1999 |
| WO | 00/09996 | 2/2000 |
| WO | 02/069791 A1 | 9/2002 |
| WO | 02/069791 | 12/2002 |
| WO | 03/017834 A1 | 3/2003 |
| WO | 2004/023125 A3 | 3/2004 |
| WO | 2005/053523 A1 | 6/2005 |
| WO | 2005/120332 A1 | 12/2005 |

OTHER PUBLICATIONS

Linderholm, P., et al., "Two-dimensional impedance imaging of cell migration and epithelial stratification", *The Royal Society of Chemistry 2006—Lab Chip, 2006*, 1155-1162.

Linderholm, P., et al., "Bipolar resistivity profiling of 3D tissue culture", *Biosensors & Bioelectronics*, 2006, 1-8.

Linderholm, P., et al., "Analytical expression for electric field between two facing strip electrodes in microchannel", *Electronics Letters*, Feb. 2, 2006, vol. 42, No. 3, 2 pages.

Linderholm, P., et al., "Resistivity probing of multilayered tissue phantoms using microelectrodes", *Institute of Physics Publishing, Physiological Measurement*, 25 (2004) 645-658.

Somersalo, E., "Layer stripping for time-harmonic Maxwell's equations with high frequency", *Inverse Problems*, 10 (1994) 449-466.

von Guggenbereg, P.A., et al., "Estimation of one-dimensional complex-permittivity profiles: a feasibility study", *Journal of Electrostatics*, 34 (1995), 263-277.

Mamishev, A. V., et al., "Uncertainty in Multiple Penetration Depth Fringing Electric Field Sensor Measurements", *IEEE Transactions on Instrumentation and Measurement*, vol, 51, No. 6, Dec. 2002, 1192-1199.

Mamishev, A. V., et al., "Development and Applications of Fringing Electric Field Dielectrometry Sensors and Parameter Estimation Algorithms", *Journal of Electrostatics*, 46 (1999) 109-123.

\* cited by examiner

METHOD AND DEVICE FOR DETERMINING A PARAMETER OF LIVING TISSUE

TECHNICAL FIELD

The invention relates to a method and a device for determining dielectric properties of living tissue, in particular but not exclusively for the purpose of measuring the glucose level in the tissue.

BACKGROUND ART

WO 02/069791 describes a device for measuring blood glucose in living tissue. It comprises an electrode arrangement with a ground electrode and a signal electrode. A signal source applies an electrical AC-signal of known voltage or current through a resistor to the electrodes, and a detector determines the voltage over the electrodes. This depends on the dielectric properties of the tissue, which, as it has been found, are indicative of the glucose level within the tissue.

Devices of this type have been found to deliver good results, but they require a substantial effort for calibration and are prone to drift, in particular when the environmental conditions change or when they are being displaced. Differential methods have been used to improve measurement accuracy in other fields of technology. Differential methods are generally based on two or more measurements, wherein one or more measurement conditions are changed between measurements. Depending on the specific application, the influence of some parameters can be eliminated or reduced by calculating the difference between the measurements.

DISCLOSURE OF THE INVENTION

Hence, it is a general object of the invention to provide a method and a device of the type mentioned above that has improved accuracy.

This object is achieved by the method and device according to the independent claims.

Hence, the device according to the invention comprises an electrode arrangement, a signal source and a detector. The signal source feeds an electrical signal to the electrode arrangement. The device is adapted to generate at least two spatially different electrical fields in the tissue. The detector measures the difference of the responses of the tissue to the electrical fields. This difference depends on the spatial difference between the electrical fields, i.e. it primarily depends on the dielectric properties of those regions within the tissue where the difference between the at least two spatially different fields is strongest.

Hence, by suitably selecting the spatial distribution of the fields, it becomes possible to primarily measure the properties of regions of the tissue that cannot be selectively measured by using a single field only.

In particular, the spatially different fields can be generated with an electrode arrangement having at least three, advantageously even more, electrodes, and by first applying a first voltage pattern to the electrodes and by then applying a second voltage pattern to the electrodes, wherein said first and said second voltage patterns are different. This can e.g. be achieved by arranging a switching assembly between the signal source and the electrodes, which selectively connects at least a first and a second pattern of the electrodes to the signal source.

In an advantageous embodiment, two values $s_1$ and $s_2$ are measured, $s_1$ being indicative of the response of the tissue to a first electrical field and $s_2$ being indicative of the response of the tissue to a second electrical field. The parameter is calculated from a weighted difference $D = k_1 \cdot s_1 - k_2 \cdot s_2$ with weights $k_1$ and $k_2$. The weights $k_1$ and $k_2$ or the ratio $k_1 : k_2$ can be calculated in a calibration procedure under the condition that the weighted difference depends only weakly on the response of the tissue near the surface of the body (i.e. in the epidermis), but primarily on the response of the tissue in a region farther away from the electrodes, i.e. deeper inside the body, such as the dermis. In other words, k1 and k2 are chosen such that the contribution of the tissue close to the electrode arrangement (i.e. of the contribution of the epidermis) to the weighted difference D is minimized; in this context, "minimized" is understood to imply that the contribution to D is considerably smaller than for the individual measured values $s_1$, $s_2$, but not necessarily zero or at an absolute minimum. This allows to minimize undesired effects (such as temperature and surface conditions) affecting the properties of the body surface. The values $s_1$ and $s_2$ may be real or complex quantities. If $s_1$ and $s_2$ are complex, $k_1$ and $k_2$ will generally be complex as well.

The device according to the invention is especially suited for measuring a glucose-level of the tissue, but it can also be used for measuring any other parameter that affects the dielectric properties of the tissue, such as an electrolyte level.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

Figure 1:
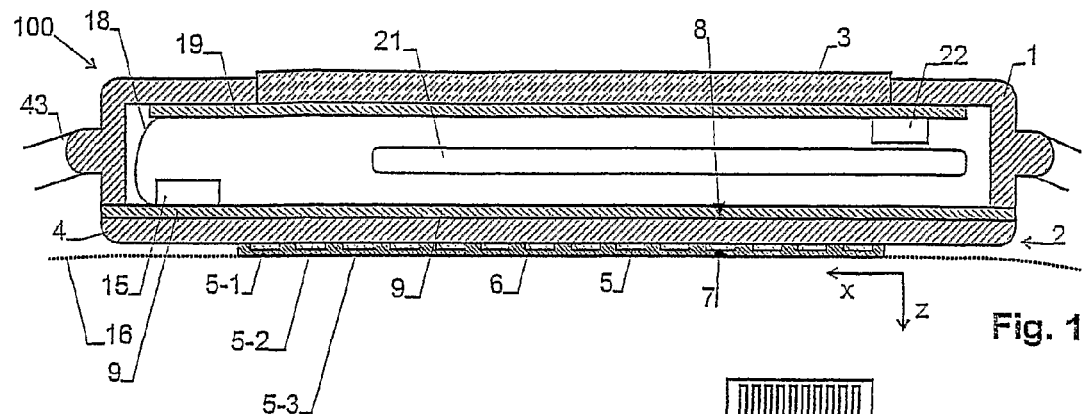
FIG. 1 is a cross section of a device for measuring a glucose level.

FIG. 1 shows a cross section of a device 100 for measuring a patient's glucose level or some other parameter in a patient's body, such as an electrolyte level of the tissue. It comprises a housing 1 closed on one side by an electrode plate 2. A display 3 is arranged opposite electrode plate 2. Electronic circuitry is arranged between electrode plate 2 and display 3.

Electrode plate 2 comprises an electrically insulating substrate 4. An electrode arrangement 5 comprising a plurality of parallel strip electrodes 5-0, 5-1, 5-2, etc. and being covered by an insulating layer 6 is arranged on an outer side 7 of insulating substrate 4. An inner side 8 of insulating substrate 4 may be covered by a ground electrode 9. Suitable through-contacts (not shown) connect the strip electrodes 5-i to contact pads arranged on inner side 8.

A first temperature sensor 15 is mounted to ground electrode 9 in direct thermal contact thereto and measures a first temperature T1.

Leads or springs 18 are provided to connect ground electrode 9, the contact pads and first temperature sensor 15 to the electronic circuitry arranged on a printed circuit board 19 forming an assembly of electronic components. A battery 21 for powering the circuitry is arranged between printed circuit board 19 and electrode plate 2. A second temperature sensor 22 can be arranged on printed circuit board 19 and in direct thermal contact thereto for measuring a second temperature T2.

Figure 2:
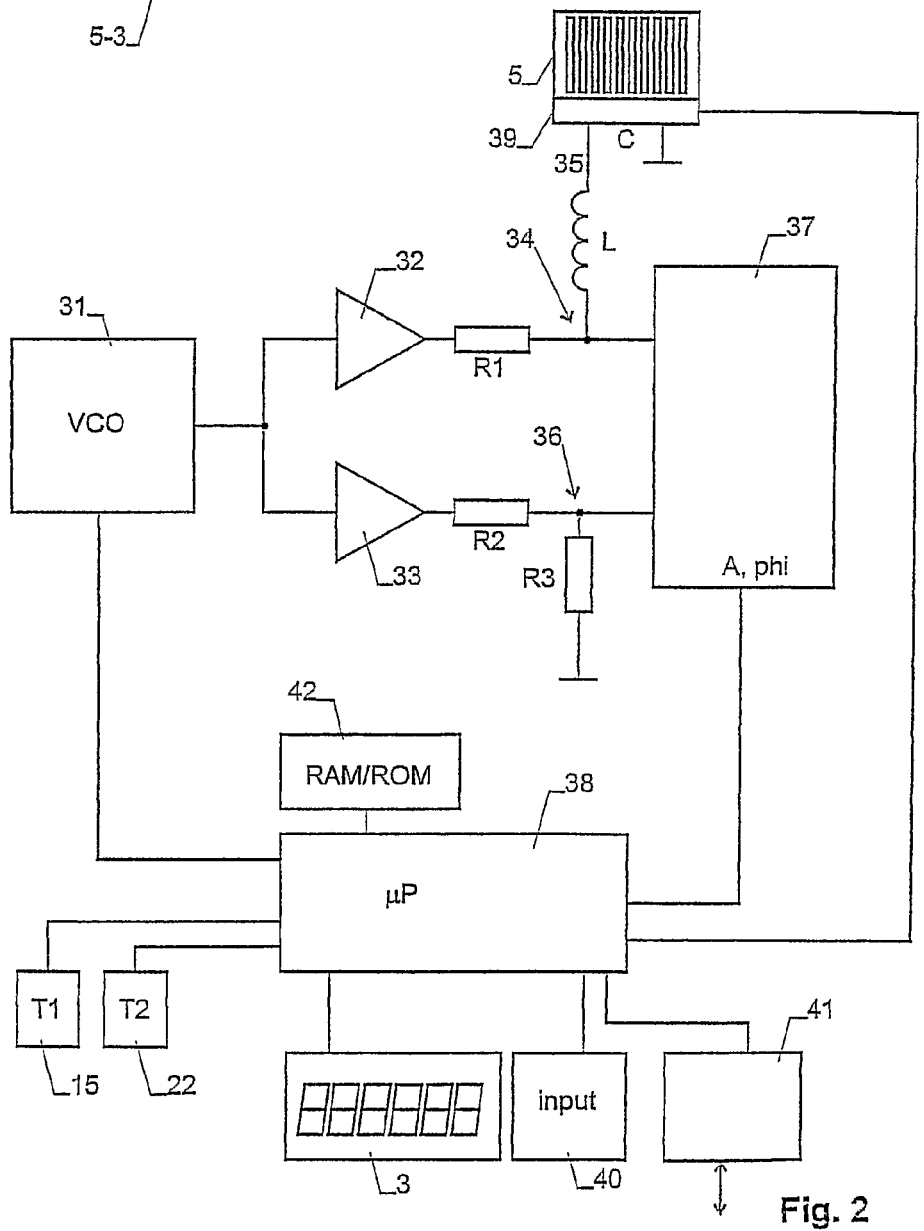
FIG. 2 is a block circuit diagram of the device of FIG. 1.

FIG. 2 shows a block circuit diagram of the circuitry of device 100. It comprises a voltage controlled oscillator (VCO) 31 as a signal source for generating a sine wave signal or another periodic signal. Instead of an oscillator, a pulse generator could be used for generating substantially non-periodic signals, such as short pulses or step-like voltage transitions. The signal from the signal source is fed to two amplifiers 32, 33. The output of first amplifier 32 is connected via a resistor R1 to a first signal path 34. A resonant circuit 35 comprising an inductance L and the capacitive load of the electrode arrangement 5 in series is connected between first signal path 34 and ground. A switching assembly 39 is used to selectively connect the strip electrodes 5-$i$ to either inductance L or ground as described below, thereby defining at least two different electrode patterns.

The output of second amplifier 33 is connected via a resistor R2 to a second signal path 36. Second signal path 36 can be substantially identical to first signal path 34 but comprises a resistor R3 as a reference load instead of resonant circuit 35.

Both signal paths 34, 36 are fed to a measuring circuit 37, which determines the relative amplitude A of both signals and/or their mutual phase shift phi. Relative amplitude A can e.g. be the amplitude of first signal path 34 in units of the amplitude of second signal path 36 (wherein the amplitudes are the peak values of the sine waves or, if pulses or voltage steps are used as measuring signal, the corresponding peak amplitude or step voltage).

The output signal of measuring circuit 37 is fed to a microprocessor 38, which also controls the operation of VCO 31.

Microprocessor 38 further samples the first and second temperature signals T1, T2 from first and second temperature sensors 15, 22. It also controls display device 3, an input device 40 with user operable controls, and an interface 41 to an external computer. A memory 42 is provided for storing calibration parameters, measurement results, further data as well as firmware for microprocessor 38. At least part of memory 42 is non-volatile.

Inductance L of the device of FIG. 2 can be generated by a coil and/or by the leads and electrodes of electrode arrangement 5. Its value is generally known with reasonable accuracy.

Electrode arrangement 5 represents a primarily capacitive load C.

The electrodes of electrode arrangement 5 are arranged on the skin 16 of the patient as shown in FIG. 1. For a good and permanent contact with the patient's skin, the device is advantageously worn on an arm or leg and provided with a suitable holder or wrist band 43.

In summary, the device shown in FIGS. 1 and 2 comprises:
an electrode arrangement 5,
a signal source (VCO 31) for applying an electrical signal to electrode arrangement 5 for generating an electrical field in the tissue,
a detector for measuring a response from the tissue to the electrical field and for determining at least one parameter therefrom, the detector primarily comprising the elements 37, 38.

Figure 3:
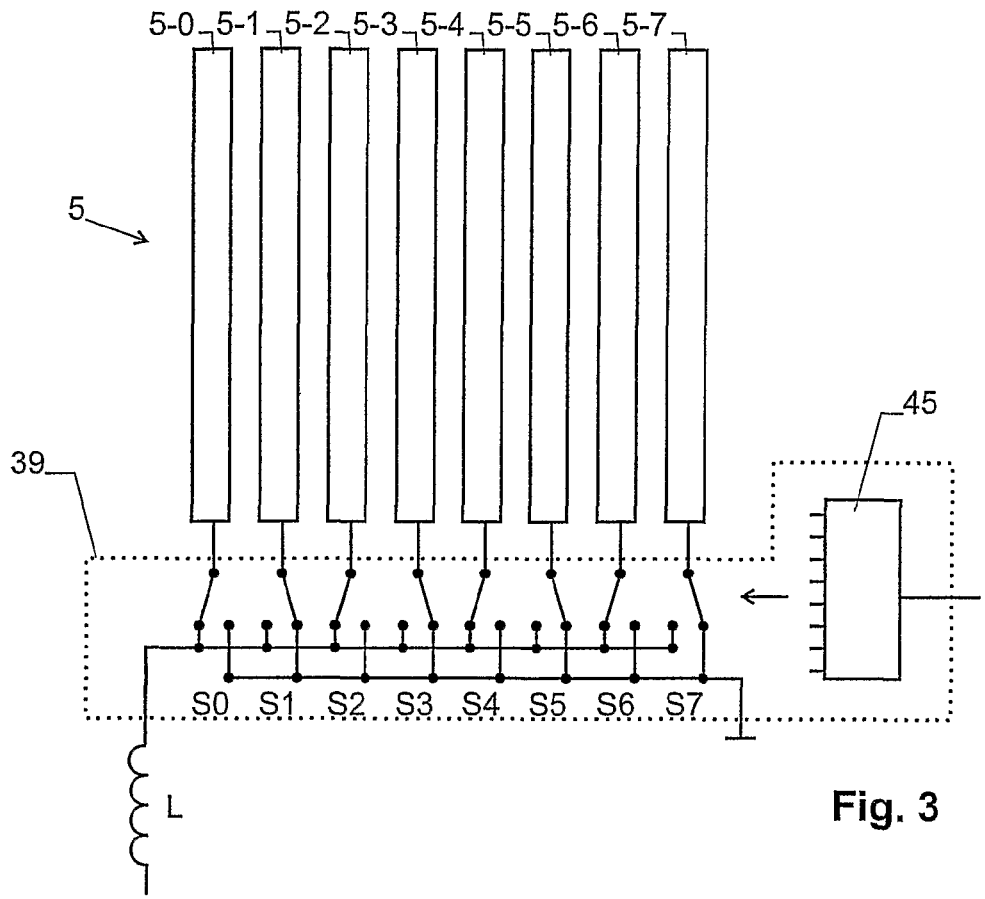
FIG. 3 is a detailed view of the electrode arrangement and the switching assembly.

FIG. 3 shows switching assembly 39 and electrode arrangement 5 in detail. As shown, each strip electrode 5-$i$ of electrode arrangement 5 is connected to an electronic switch S1 for selectively connecting it either to ground or to inductance L. A switch control unit 45 is provided for individually controlling the position of each the switches S1. Switch control unit 45 is controlled by microprocessor 38.

In the present embodiment, switch control unit 45 has two modes of operation.

In the first mode of operation (as it is shown by the switch positions of FIG. 3), switch control unit 45 sets switches S0, S2, S4 and S6 to connect electrodes 5-0, 5-2, 5-4 and 5-6 to inductance L and thereby to the signal from VCO 31, while switches S1, S3, S5, S7 are set to connect electrodes 5-1, 5-3, 5-5 and 5-7 to ground. In this first mode of operation, the voltage pattern applied to the electrodes is therefore such that each pair of neighboring electrodes carry different voltages.

Figure 4:
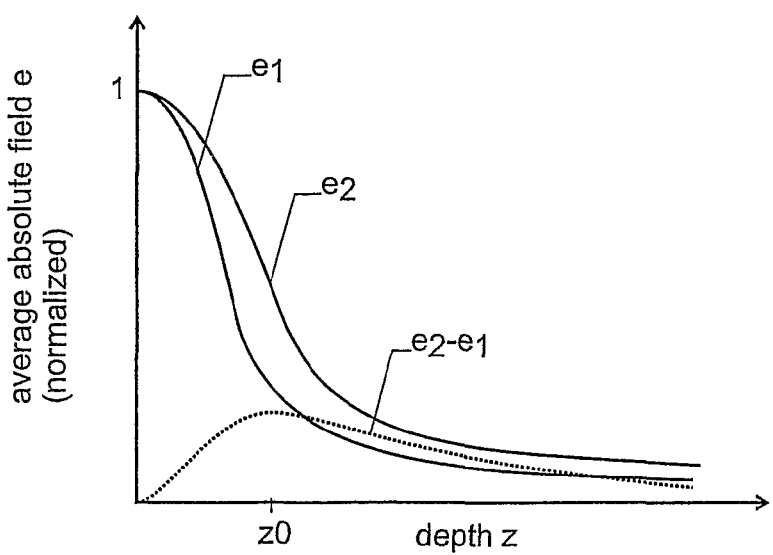
FIG. 4 shows normalized, average absolute fields as a function of depth.

In the second mode of operation, switches S0, S1, S4 and S5 are set to connect electrodes 5-0, 5-1, 5-4 and 5-5 to inductance L and thereby to the signal from VCO 31 while switches S2, S3, S6 and S7 are set to connect electrodes 5-2, 5-3, 5-6 and 5-7 to ground. In this mode of operation, the voltage pattern at the electrodes of a first part of the pairs of neighboring electrodes carry equal voltages and the electrodes of a second part of the pairs of neighboring electrodes carry different voltages. As will be easily understood, the electric fields generated in the two modes of operation will have different spatial distribution, as illustrated by curves e1, e2 of FIG. 4. Any measured parameter s describing the response of the tissue to the applied field will depend on how the field is distributed and will have different values $s_1$ and $s_2$ in the two modes of operation.

In the present context, it is of particular interest how the measured parameter s depends on the dielectric properties of the epidermis close to the surface and how it depends on the dielectric properties of the dermis deeper in the tissue.

In the following, we assume that the measured parameter s is the capacitance $C_i$ of electrode arrangement 5 for a given mode of operation i. In linear approximation, we can write $$C_i(\varepsilon_{ep}, \varepsilon_{dr}) \approx C_i(\varepsilon_{ep}^0, \varepsilon_{dr}^0) + (\varepsilon_{ep}^0 - \varepsilon_{ep})\frac{\partial C_i}{\partial \varepsilon_{ep}}\bigg|_{\varepsilon_{ep}^0} + (\varepsilon_{dr}^0 - \varepsilon_{dr})\frac{\partial C_i}{\partial \varepsilon_{dr}}\bigg|_{\varepsilon_{dr}^0}, \quad (1)$$

where subscript "ep" denotes contributions from the epidermis and "dr" contributions from the dermis. Superscript "0" denotes "normal" (unperturbed) values, e.g. at the time of a calibration measurement or for a typical subject. $\in$ is the dielectric constant of the tissue in the dermis or epidermis, respectively. The derivatives of C in view of $\in$ can e.g. be calculated from a dielectric model of typical tissue. A similar dependence will be observed for other measured values, such as the inverse resistance 1/R between the electrodes versus conductivities of dermis and epidermis or the complex impedance Z as function of both dielectric constants and conductivities in dermis and epidermis. Again, the measured value will depend on the mode of operation, i.e. on the voltage pattern applied to the electrodes.

In operation, device 100 can e.g. be used to measure the capacitance C, resistance R or complex impedance Z of electrode arrangement 5 at one or more frequencies f. This impedance Z depends on the dielectric response of the tissue to the applied electric field and, as it has been found, it is indicative of the glucose concentration in the tissue.

As it is known to the person skilled in the art, capacitance C, resistance R or impedance Z can e.g. be measured by determining the relative amplitude A and phase shift phi provided by measuring circuit 37.

Advantageously, microprocessor 38 computes two values $s_1$ and $s_2$ indicative of the dielectric response of the tissue to the first and the second electric field. If the capacitance $C_1$ and $C_2$ in the first and the second mode of operation are measured, we have $s_1 = C_1$ and $s_2 = C_2$.

Subsequently, the difference of the responses to the two electric fields is determined, advantageously by calculating the weighted difference $$D^c = k_1 \cdot C_1 - k_2 \cdot C_2, \quad (2)$$

where the subscript C denotes that we are talking about constants $k_1$, $k_2$ for the measurement of capacitance (a similar equation with different constants can be derived for the measurement of the conductance, i.e. s=1/R), where the weights $k_1$ and $k_2$ are chosen such that the non-constant contributions of the dielectric properties of the epidermis to the difference D are substantially 0.

Combining Equations (1) and (2), we obtain $$D^C \approx \lfloor k_1^C C_1(\varepsilon_{ep}^0, \varepsilon_{dr}^0) - k_2^C C_2(\varepsilon_{ep}^0, \varepsilon_{dr}^0) \rfloor + \quad (3)$$
$$(\varepsilon_{ep}^0 - \varepsilon_{ep}) \left[ k_1^c \frac{\partial C_1}{\partial \varepsilon_{ep}} \bigg|_{\varepsilon_{ep}^0} - k_2^c \frac{\partial C_2}{\partial \varepsilon_{ep}} \bigg|_{\varepsilon_{ep}^0} \right] +$$
$$(\varepsilon_{dr}^0 - \varepsilon_{dr}) \left[ k_1^c \frac{\partial C_1}{\partial \varepsilon_{dr}} \bigg|_{\varepsilon_{dr}^0} - k_2^c \frac{\partial C_2}{\partial \varepsilon_{dr}} \bigg|_{\varepsilon_{dr}^0} \right]$$

In order to minimize the non-constant epidermis contributions, the value of the second square bracket in Eq. (3) should be 0. This can e.g. be achieved by arbitrarily setting $k_1^c$ to 1 and using $k_2^c = (\partial C_1/\partial \in_{ep})/(\partial C_2/\partial \in_{ep})$.

Instead of arbitrarily setting $k_1^c$ to 1, the constants can be chosen such that the contribution from the "normal" values in the first square bracket of Eq. (3) becomes 0 as well, thus making the difference D dependent on the dermis contributions only. In that case, setting the first and the second square bracket in Eq. (3) to 0 will yield a system of two equations that allows to determine the values of $k_1^c$ and $k_2^c$. After measuring the difference D as well as the temperatures $T_1$ and $T_2$, microprocessor 38 can e.g. use a formula of type $$g = F(D, T_1, T_2, a_0, \ldots a_M) \quad (4)$$

for determining the glucose level g (or a parameter indicative thereof) from the measured input values D, $T_1$ and $T_2$, where the function F has M+1 parameters $a_0, \ldots a_M$ (M≧0).

The function F can be empirical or it can be based at least partially on a model describing the physical nature of the mechanisms involved.

Assuming that the relation between the glucose level g and the measured values $s_i$ is linear at least in approximation, we can use $$g = a_0 + a_1 \cdot D + a_2 \cdot T_1 + a_3 \cdot T_2 \quad (5)$$

with M=3.

In order to determine the parameters $a_0, a_1 \ldots a_M$, a series of at least M+1 calibration measurements has to be carried out, each calibration measurement comprising a determination of the input values D, $T_1$ and $T_2$ and a reference glucose level g measured by conventional means, e.g. by an invasive method.

In a most simple approach, the parameters $a_i$ can then be obtained from a conventional least-squares fitting algorithm that varies the parameters $a_i$ in order to find a best match of equations (4) or (5) to the calibration measurements. Suitable algorithms are known to a person skilled in the art and are e.g. described by Press, Teukolsky, Vetterling and Flannery in "Numerical Recipes in C", Cambridge University Press, $2^{nd}$ edition, 1992, Chapter 15.

Once the parameters $a_i$ are known, the glucose level g can be determined from equations (4) or (5) based on the measurement of the input values D, T1 and T2.

Re-calibration of at least part of the parameters may be advisable at regular intervals or after a displacement of device 100 in respect to the specimen.

In the above example, the electrode arrangement comprises a plurality of strip-shaped electrodes arranged side by side. The number of electrodes may vary, even though a number of at least three electrodes is required in order to support at least two spatially different electrode patterns. At least four, in particular at least eight electrodes is advantageous in order to keep fringe field effects small.

The voltage pattern to be applied to the electrodes in the different modes of operation can vary as well. In the example above, the following scheme was used: In the first mode of operation, the voltage $v_i$ at the electrode i was $$v_i = v_0 \quad \text{if } i \text{ is even} \quad (6)$$
$$= 0 \quad \text{otherwise,}$$

(where $v_0$ denotes the voltage at the output of inductance L) while in the second mode of operation the voltage at electrode i was $$v_i = v_0 \quad \text{if floor}(i/2) \text{ is even} \quad (7)$$
$$= 0 \quad \text{otherwise,}$$

where floor(x) is equal to x if x is an integer value or the next lower integer value otherwise.

It must be noted, though, that other patterns can be used as well. For example, instead of two, three or more neighboring electrodes can be applied to the same voltage in the second mode of operation. It may also be advisable to make sure that the outermost electrodes are always connected to ground in order to have well defined boundary conditions.

Other voltage patterns can be used as well. In order to emphasize the difference of the fields far from the electrodes, i.e. the difference of the contributions from the dermis, it is also be possible to use more than two possible voltage levels. For example, in the second mode of operation, the voltage at electrode $v_i$ can be chosen to be $$v_i = v_0 \cdot \sin(i \cdot \pi/k), \quad (8)$$

with k≧2. For example, for k=2, the voltage at electrode 0 is 0, at electrode 1 it is $v_0$, at electrode 2 it is 0, at electrode 3 it is $-v_0$, etc., which leads to an increase of the field at some distance from the electrodes as compared to the field close to the electrodes.

In general, any electrode arrangement can be used that is able to generate at least two spatially different alternating fields in the adjacent tissue. "Spatially different" is used to describe fields that have different shape. Fields that merely differ by a multiplicative factor are not understood to be "spatially different".

While there are shown and described presently preferred embodiments of the invention, it is to be distinctly understood that the invention is not limited thereto but may be otherwise variously embodied and practiced within the scope of the following claims.

The invention claimed is:

1. A device for measuring a parameter of living tissue, which parameter affects a response of said tissue to an electric field, comprising an electrode arrangement (5),
a signal source (31) generating an electrical signal to be applied to said electrode arrangement (5) for generating an electrical field in said tissue, and
a detector (37, 38) for measuring a response from said tissue to said electrical field and for determining at least one parameter therefrom,
wherein said device is adapted to generate at least two spatially different electrical fields ($E_1$, $E_2$) in said tissue, and wherein said detector is adapted to determine said parameter from a difference of the responses of said tissue to said spatially different electrical fields,
and further comprising a switching assembly (39) arranged between said signal source (31) and said electrodes (5-$i$) for selectively connecting at least a first and a second pattern of said electrodes (5-$i$) to said signal source (31).

2. The device of claim 1, wherein said parameter is a glucose level in the tissue.

3. A device for measuring a parameter of living tissue, which parameter affects a response of said tissue to an electric field, comprising
an electrode arrangement (5),
a signal source (31) generating an electrical signal to be applied to said electrode arrangement (5) for generating an electrical field in said tissue, and
a detector (37, 38) for measuring a response from said tissue to said electrical field and for determining at least one parameter therefrom,
wherein said device is adapted to generate at least two spatially different electrical fields ($E_1$, $E_2$) in said tissue, and wherein said detector is adapted to determine said parameter from a difference of the responses of said tissue to said spatially different electrical fields,
wherein said electrode arrangement (5) comprises a plurality of electrodes (5-$i$) arranged side by side, and
wherein said device is adapted to selectively apply
in a first mode of operation, a first voltage pattern to said electrodes (5-$i$), wherein in said first voltage pattern the electrodes of each pair of neighboring electrodes carry different voltages, and
in a second mode of operation, a second voltage pattern to said electrodes (5-$i$), wherein in said second voltage pattern the electrodes of a first part of the pairs of neighboring electrodes carry equal voltages and the electrodes of a second part of the pairs of neighboring electrodes carry different voltages.

4. The device of claim 3, wherein said electrode arrangement (5) comprises at least four electrodes (5-$i$) arranged side by side.

5. The device of claim 3, wherein said parameter is a glucose level in the tissue.

6. A device for measuring a parameter of living tissue, which parameter affects a response of said tissue to an electric field, comprising
an electrode arrangement (5),
a signal source (31) generating an electrical signal to be applied to said electrode arrangement (5) for generating an electrical field in said tissue, and
a detector (37, 38) for measuring a response from said tissue to said electrical field and for determining at least one parameter therefrom,
wherein said device is adapted to generate at least two spatially different electrical fields ($E_1$, $E_2$) in said tissue, and wherein said detector is adapted to determine said parameter from a difference of the responses of said tissue to said spatially different electrical fields,
wherein detector (37, 38) is adapted to measure a first value $s_1$ indicative of the response of said tissue to a first electrical field and a second value $s_2$ indicative of the response of said tissue to a second electrical field, wherein said first and said second electrical fields are spatially different, and
to calculate a weighted difference $k1 \cdot s1 - k2 \cdot s2$ with weights k1 and k2, wherein the weights are chosen such that a non-constant contribution of the di-electric response of an epidermis of the tissue to the weighted difference is minimized.

7. The device of claim 6, wherein said parameter is a glucose level in the tissue.

* * * * *